US007741509B2

(12) United States Patent
Cook et al.

(10) Patent No.: US 7,741,509 B2
(45) Date of Patent: *Jun. 22, 2010

(54) CONVERSION OF TEREPHTHALIC ACID TO DI-N-BUTYL TEREPHTHALATE

(75) Inventors: Steven Leroy Cook, Kingsport, TN (US); Phillip Wayne Turner, Blountville, TN (US); Vickie Haygood Osborne, Fall Branch, TN (US)

(73) Assignee: Eastman Chemical Company, Kingsport, TN (US)

( * ) Notice: Subject to any disclaimer, the term of this patent is extended or adjusted under 35 U.S.C. 154(b) by 446 days.

This patent is subject to a terminal disclaimer.

(21) Appl. No.: 11/732,236

(22) Filed: Apr. 3, 2007

(65) Prior Publication Data

US 2008/0183012 A1 Jul. 31, 2008

Related U.S. Application Data

(63) Continuation-in-part of application No. 11/699,652, filed on Jan. 30, 2007.

(51) Int. Cl.
C07C 69/76 (2006.01)
(52) U.S. Cl. ........................................ 560/98
(58) Field of Classification Search ............ 560/98
See application file for complete search history.

(56) References Cited

U.S. PATENT DOCUMENTS

| 1,944,887 | A | * | 1/1934 | De Witt Graves ............ 554/1 |
| 2,124,605 | A | * | 7/1938 | Bousquet .................. 570/258 |
| 2,459,014 | A | * | 1/1949 | Lufkin et al. ............... 560/98 |
| 2,479,066 | A | * | 8/1949 | Gresham .................... 560/98 |
| 2,491,660 | A | * | 12/1949 | Gresham .................... 560/99 |
| 2,579,329 | A | * | 12/1951 | Martin ..................... 568/764 |
| 2,802,861 | A | * | 8/1957 | De Jonge et al. ............ 560/98 |
| 2,975,209 | A | | 3/1961 | Bos et al. |
| 3,155,715 | A | * | 11/1964 | Ardis et al. ................ 560/98 |
| 3,250,801 | A | * | 5/1966 | Stange et al. ............... 560/95 |
| 4,380,677 | A | * | 4/1983 | Kurek ..................... 568/788 |
| 4,654,436 | A | | 3/1987 | Lane et al. |
| 4,675,434 | A | | 6/1987 | Uhm et al. |
| 5,138,025 | A | * | 8/1992 | Mossman .................. 528/298 |
| 5,326,864 | A | | 7/1994 | Besemer et al. |
| 5,391,770 | A | | 2/1995 | Le Fur et al. |
| 5,532,495 | A | | 7/1996 | Bloomquist et al. |
| 5,571,387 | A | * | 11/1996 | Marker et al. ............... 203/41 |
| 5,585,527 | A | * | 12/1996 | Marker ..................... 203/18 |
| 6,841,505 | B2 | | 1/2005 | Eng |
| 7,276,621 | B2 | | 10/2007 | Cook et al. |
| 2002/0028963 | A1 | | 3/2002 | Gubisch et al. |
| 2004/0030175 | A1 | | 2/2004 | Disteldorf et al. |
| 2007/0161815 | A1 | * | 7/2007 | Osborne et al. ............. 560/76 |

FOREIGN PATENT DOCUMENTS

| GB | 733 322 | 7/1955 |
| GB | 878269 | 9/1961 |
| JP | 60 004151 | 1/1985 |
| JP | 2001 031794 | 2/2001 |
| JP | 2003238479 | 8/2003 |
| JP | 2005 120019 A2 | 5/2005 |
| JP | 2005 306759 A2 | 11/2005 |
| RU | 2 114 100 C1 | 6/1998 |
| WO | WO 2007/021475 A2 | 2/2007 |

OTHER PUBLICATIONS

Zeng, Chongyu; "Study on esterification rule in DOTP preparation"; XP0024138167 retrieved from STN Database accession No. 1995:468078; Chemical Abstracts Service, Columbus, Ohio.
Jiang, Pinping; "Synthesis of DOTP plasticizer by esterification"; XP002413816 retrieved from STN Database accession No. 1995:454573; Chemical Abstracts Service, Columbus, Ohio.
Meiqi, Fu; "A Technique of Producing Dioctyl Terephthalate and an Improvement in the Technique"; Tianjin Chemical Industry, China, vol. 20, No. 17, 2006.
Mekhtiev, S. D. et al.; "Esterification of terephthalic and isophthalic acids by aliphatic alcohols"; Azerbaidzhanskii Khimicheskii Zhurnal; vol. 3; 1965; pp. 67-72.
Yoneda, Shigeo et al.; "Organic synthesis by use of inorganic salts. XII. Preparation of esters of carboxylic acids in dimethylformamide"; Kogyo Kagaku Zasshi; 69(4); 1966; pp. 641-643.
Roberts, Carleton W. et al.; The synthesis of and the dye-sensitized photoinitiated decompositions of monomolecular analogs of poly-(ethylene terephthalate); Clemson University Review of Industrial Management and Textile Science; 15(1); 1976; pp. 13-35.
Notification of Transmittal of the International Search Report and the Written Opinion of the International Searching Authority, or the Declaration date of mailing Feb. 16, 2007 received in the International Application No. PCT/US2006/028942.
Office Action date of mailing Jul. 10, 2007 received on co-pending U.S. Appl. No. 11/699,652.
Office Action date of mailing Jun. 11, 2008 received on co-pending U.S. Appl. No. 11/699,652.
Notification of Transmittal of the International Search Report and the Written Opinion of the International Searching Authority, or the Declaration date of mailing Jun. 25, 2008 received in the International Application No. PCT/US2008/008355.
Notification of Transmittal of the International Search Report and the Written Opinion of the International Searching Authority, or the Declaration date of mailing Jul. 2, 2008 received in the International Application No. PCT/US2008/000503.

\* cited by examiner

Primary Examiner—Shailendra Kumar
(74) Attorney, Agent, or Firm—Brett L Nelson; Bernard J. Graves, Jr.

(57) ABSTRACT

Disclosed is a process for the preparation of di-n-butyl terephthalate by the esterification of terephthalic acid with n-butanol in the presence of a strong acid while employing a fractionating column.

3 Claims, 1 Drawing Sheet

CONVERSION OF TEREPHTHALIC ACID TO DI-N-BUTYL TEREPHTHALATE

CROSS-REFERENCE TO RELATED APPLICATION

This application is a continuation-in-part of U.S. patent application Ser. No. 11/699,652 filed on Jan. 30, 2007, the disclosure of which is incorporated herein by reference in its entirety.

FIELD OF THE INVENTION

This invention pertains to the preparation of di-n-butyl terephthalate (DBT) from terephthalic acid (TPA).

BACKGROUND OF THE INVENTION

Terephthalic acid di-esters, such as Di-n-butyl terephthalate, also known as DBT, can be used as plasticizers in a variety of polymeric materials such as polyvinyl chloride. Eastman Chemical Company produces di(2-ethylhexyl) terephthalate, also known as DOTP or 168 Plasticizer, by the titanate-catalyzed transesterification of dimethyl terephthalate (DMT) with 2-ethylhexanol. A more direct route to this product has been described in parent U.S. patent application Ser. No. 11/699,652 wherein terephthalic acid (TPA) is reacted with 2-ethylhexanol using a titanate catalyst, with reaction condition involving either pressure or ambient pressure through use of a fractionating column. However, titanate catalyst cannot be used directly to produce di-n-butyl terephthalate (DBT). The present inventors have discovered that excess strong acids, such as methane sulfonic acid and sulfuric acid, in combination with a fractionating column overcome this problem.

BRIEF SUMMARY OF THE INVENTION

An embodiment of the present invention concerns a process for the preparation of di-n-butyl terephthalate. The method comprises contacting terephthalic acid (TPA) with n-butanol in the presence of a catalyst in a reactor, wherein the total pressure is maintained at about atmospheric pressure, the temperature is maintained at about 110° to 220° C., and the reactor is fitted with a fractionating column for removing water.

The process according to the present invention provides the desired di-n-butyl terephthalate product at good reaction rates with high conversions of the TPA reactant with no observable foaming problems.

BRIEF DESCRIPTION OF THE DRAWING

The figure shows a reactor and column useful with the process according to the present invention.

DETAILED DESCRIPTION

Figure 1:
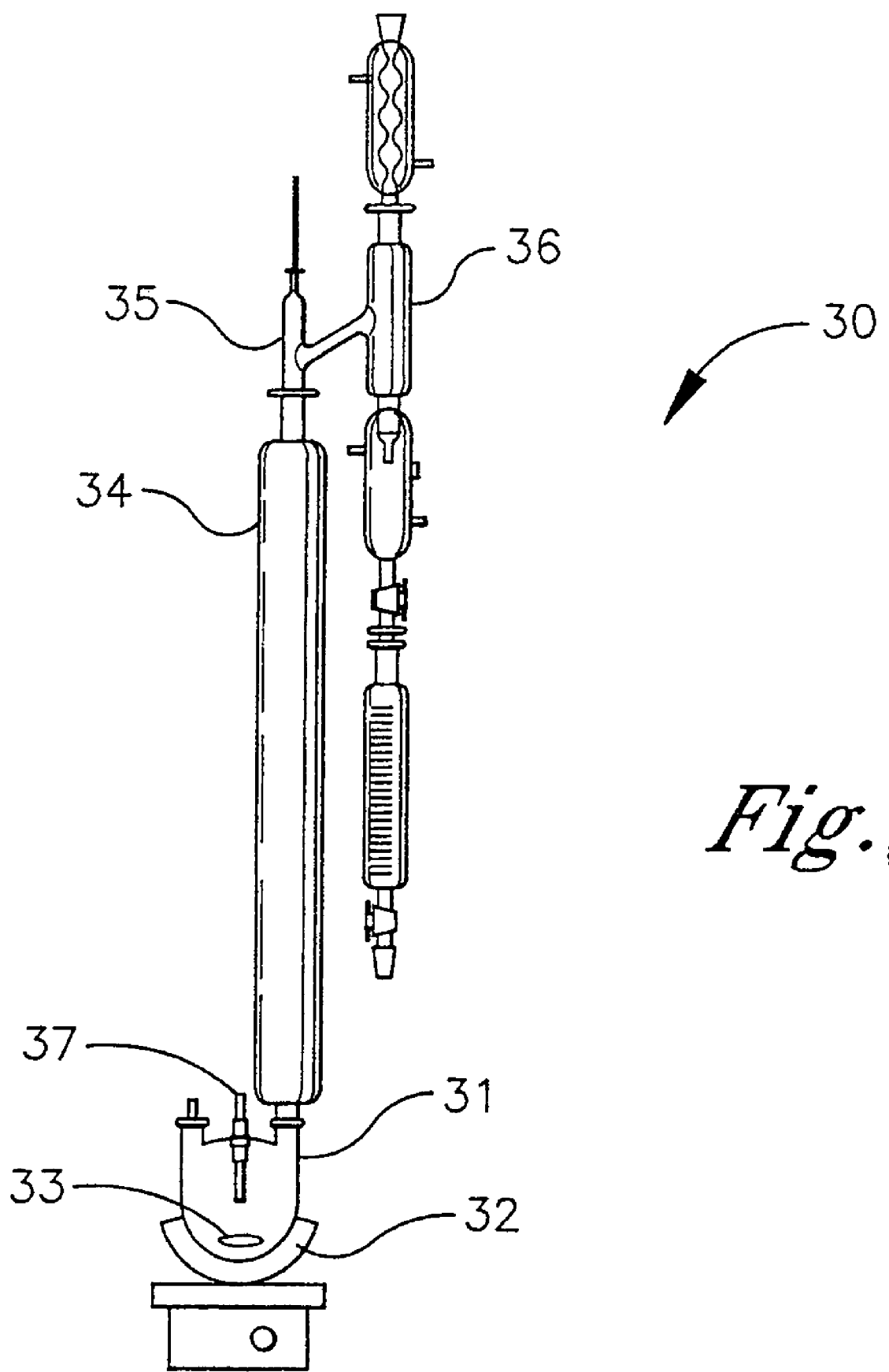

According to the present invention, a batch or continuous reactor can be used for the direct conversion of TPA to di-n-butyl terephthalate (DBT) at normal pressure and temperature. The reactor can be a simple, stirred unit fitted with a fractionation column for water removal (and thus would not require the use of inert gas for removing water) or can contain multiple ports for reactant introduction and product removal. For example, the reactor can be fitted with a fractionation column and access ports for charging TPA, alcohol (n-butanol) and catalyst. The efficiency of the fractionating column can range from as many as 35 stages, to as few as two stages, but less stages results in foaming to the extent that operation of the process becomes difficult. In practice, the reactor is charged with terephthalic acid, excess alcohol, and a catalytic amount of a catalyst. Heating and stirring the mixture to reflux results in efficient removal of water and esterification of the TPA to DBT. The volatile components chiefly consist of the water of reaction and unreacted n-butanol. The water can be separated via a decanter, and the alcohol is allowed to reflux throughout the column. Conversion to DBT is essentially complete in four to five hours and is evident by the disappearance of the highly insoluble TPA. The crude product is then neutralized with 2.5% NaOH and decanted. Excess n-butanol is stripped off at reduced pressure. The product is purified by distillation at reduced pressure. A second 2.5% NaOH wash is performed, followed by phase separation and drying at reduced pressure.

In an example of this embodiment, the number of fractionating stages is in the range of three high-efficiency theoretical stages (HETS) to six HETS, with an exemplary number to minimize foaming in the range of four to five HETS. The amount of excess n-butanol is in the range of 25 mole percent to 400 mole percent, with an exemplary amount of 100 mole percent to facilitate conversion to diester. Unreacted alcohol can be readily recycled to the process. Suitable catalysts include but are not limited to methane sulfonic acid, sulfuric acid, methane disulfonic acid, butane sulfonic acid, and perfluorobutane sulfonic acid. These catalysts can be used individually or in combination of two or more thereof. The range of catalyst concentration can be about 1% to about 15%, about 3% to about 10% or even about 5% base on the total charge of TPA and butanol. The process may be practiced in the continuous mode by adding the TPA to a suitable reactor by means of a screw feeder and the butanol/catalyst as a pump-fed mixture to a stirred, reactor equipped with a fractionating column/decanter combination such that the water of reaction can be removed and the unreacted alcohol returned to the reactor. The effluent from this reactor can be passed to a chain of one or more finishing reactors wherein the conversion to terephthalic acid diester with removal of water is continued. The product of this reaction can be further processed and refine by steps that are compatible with those listed for the batch example.

In this embodiment, the pressure can be maintained at about atmospheric pressure. Moreover, temperature within the reaction zone can be maintained at a range of about 10° to 220° C., with an exemplary temperature range of between about 115° to 140° C. Alternatively, pressurized reactor systems and higher reaction temperatures could be employed for the purpose of accelerating the reaction rate.

EXAMPLES

The process according to the embodiments described above is further illustrated by the following examples wherein all percentages given are by weight unless specified otherwise.

Example 1

The equipment consisted of a two-liter base fitted with a heating mantel, magnetic stir bar, temperature sensor, decanter, and distillation column. The attached column consisted of a Penn-State-packed column with 10 inches of packing, which typically yields approximately five high-efficiency theoretical stages of separation. The top of the decanter was fitted with a condenser to allow the water-n-butanol azeotrope to condense and collect in the decanter. The top n-butanol layer was returned to the column via an overflow tube, and the water collected for weighing.

The base was charged with 370.6 g (5 mole; 25 mole percent excess) n-butanol, 332.3 g (2 mole) TPA, and 0.15 g (213 ppm) TIPT catalyst and the mixture heated. After 4.5 hours at reflux (117° C.) no water had formed (72 g theoretical).

After 4.5 hours, began decanting n-butanol out of the decanter attempting to increase the base temperature. Removed 177 g n-butanol over the next 1.5 hours, stirring failed. When stirring was resumed, charged 2 drops of sulfuric acid and held and an additional 1.5 hours, less than 1 ml of water formed, discarded the batch.

Example 2

The equipment consisted of a two-liter base fitted with a heating mantel, magnetic stir bar, temperature sensor, decanter, and distillation column. The attached column consisted of a Penn-State-packed column with 10 inches of packing. The top of the decanter was fitted with a condenser to allow the water-n-butanol azeotrope to condense and collect in the decanter. The top n-butanol layer was returned to the column via an overflow tube, and the water collected for weighing.

The base was charged with 300 g DBT, 370.6 g (5 mole; 25 percent mole excess) n-butanol, 332.3 g (2 mole) TPA, and 0.2 g (199 ppm) TIPT catalyst and the mixture was heated. This reaction held reflux at 122° C., began removing n-butanol from the decanter (approximately 50 g/thirty minutes) in an attempt to increase the base temperature. The reaction was held for 6.0 hours with no water forming (72 g theoretical), discarded batch.

A total of 329.2 g of n-butanol were removed starting thirty minutes into the reaction through 4.5 hours into the reaction. The base temperature ramped from 122° C. to 138° C. until the final 57.2 g of n-butanol were removed. Let stir an additional 1.5 hours with the base temperature ramping to a final temperature of 187° C. The take-off temperature remained 117° C. throughout reaction.

Example 3

The equipment consisted of a one-liter base fitted with a heating mantel, over head stirrer, temperature sensor, distillation column, decanter, and n-butanol feed pump. The attached column consisted of a Penn-State-packed column with 10 inches of packing. The top of the decanter was fitted with a condenser to allow the water-n-butanol azeotrope to condense and collect in the decanter. The top n-butanol layer was returned to the column via an overflow tube, and the water collected for weighing.

The base was charged with 150.0 g DBT, 166.2 g (1 mole) TPA, and 0.1 g (318 ppm) TIPT catalyst and the mixture was heated. Maintaining a pot temperature of 200° C., began subsurface addition of n-butanol. The total feed time was eight hours with a total of 75 ml n-butanol fed to the base. No water was formed during this reaction (36 g theoretical). Discarded batch.

Example 4

The equipment consisted of a one-liter base fitted with a heating mantel, over head stirrer, temperature sensor, decanter, and n-butanol feed pump. The top of the decanter was fitted with a condenser to allow the water-n-butanol azeotrope to condense and collect in the decanter. The top n-butanol layer was returned to the column via an overflow tube, and the water collected for weighing.

The base was charged with 150.0 g DBT, 166.2 g (1 mole) TPA, and 17.6 g (5% by weight) p-TSA catalyst and the mixture was heated. A pot temperature of 150° C. was maintained and subsurface addition of n-butanol started. Three hours into the reaction, only 0.8 g of water had been captured, increased the pot temperature to 160° C. for the remainder of the reaction time. The total feed time was fourteen hours with a total of 163 ml n-butanol fed to the base. A total of 17.3 g of water was removed during the subsurface addition (36 g theoretical). The pot still contained a large amount of solids. Discarded the batch.

Example 5

The equipment consisted of a one-liter base fitted with a heating mantel, over head stirrer, temperature sensor, decanter, and n-butanol feed pump. The top of the decanter was fitted with a condenser to allow the water-n-butanol azeotrope to condense and collect in the decanter. The top n-butanol layer was returned to the column via an overflow tube, and the water collected for weighing.

The base was charged with 150.0 g DBT, 166.2 g (1 mole) TPA, and 35.2 g (11% by weight of initial charge as catalyst and co-solvent) phosphoric acid catalyst and the mixture was heated. Upon addition of phosphoric acid to the DBT, the mixture turned to a white slurry. This slurry congealed temporarily when TPA was charged, then dispersed upon addition of heat. A pot temperature of 200° C. was maintained, and subsurface addition of n-butanol was started. The feed time was nine hours with a total of 305 ml of n-butanol fed subsurface. The total amount of water removed was 70.4 g (theoretical 36 g).

The mixture was charged to a two-liter drop bottom flask and held at 80° C. At this temperature the mixture was neutralized with 5% sodium hydroxide wash and stirred for thirty minutes at temperature. The agitation was then stopped and the reactor contents allowed to settle. The mixture formed three layers; the lower layer was a solid, then water layer, and the upper layer small organic. The batch was discarded.

Example 6

The equipment consisted of a one-liter base fitted with a heating mantel, over head stirrer, temperature sensor, decanter, and n-butanol feed pump. The top of the decanter was fitted with a condenser to allow the water-n-butanol azeotrope to condense and collect in the decanter. The top n-butanol layer was returned to the column via an overflow tube, and the water collected for weighing.

The base was charged with 150.0 g DBT, 166.2 g (1 mole) TPA, 31.4 g (10% by weight of initial charge as co-solvent) DMSO, and 3.1 g (1% by weight as catalyst) MSA and the mixture heated to 200° C. At temperature, began subsurface addition of n-butanol. Upon addition of the n-butanol, the pot temperature dropped, and 16 ml of n-butanol was found to decrease pot temperature to 187° C. This reaction was attempted 4.5 hours. The total water removed was 9.6 g (theoretical 36 g), and 1.4 g removed in the 1.5 hours with the pot temperature dropping to 171° C. The total amount of n-butanol fed to the reactor subsurface was 86 ml. A large amount of solids in remained in the pot. The batch was discarded.

Example 7

The equipment consisted of a one-liter base fitted with a heating mantel, overhead stirrer, temperature sensor, and decanter. The top of the decanter was fitted with a condenser to allow the water-n-butanol azeotrope to condense and collect in the decanter. The top n-butanol layer was returned to the column via an overflow tube, and the water collected for weighing.

The base was charged with 185.3 g (25% excess) n-butanol, 166.2 g (1 mole) TPA, 35.2 g (10% by weight of initial charge as co-solvent) DMSO, and 3.5 g (1% by weight as catalyst) MSA and the mixture was heated to reflux (115° C.). This reaction was held for four hours at reflux, there was no water removed during reaction step (theoretical 36 g). This batch was discarded.

Example 8

The equipment consisted of a one-liter base fitted with a heating mantel, over head stirrer, temperature sensor, Dean-Stark trap, and sparge line for subsurface nitrogen feed. The top of the flask was fitted with a condenser to allow the water-n-butanol azeotrope to condense and collect in the decanter. The top n-butanol layer was returned to the column via an overflow tube, and the water collected for weighing.

The base was charged with 89.0 g (1.2 mole; half of the 50% excess normally used in order to increase reaction temperature), n-butanol, 133.0 g (0.80 mole) TPA, and 9.3 g (3% by weight) MSA catalyst. The mixture was heated to reflux while sparging nitrogen subsurface. After 11.5 hours of reaction, solids were still present in the reaction. The temperature of the pot remained at 120° C. or less for the first four hours of the reaction. The temperature would slowly climb, but this did not appear to improve the reaction rate. When more butanol was added, the base temperature did not increase above 120° C. Total water removed was 10.6 g (theoretical 36 g). This batch was discarded, solids still present.

Example 9

The equipment consisted of a one-liter base fitted with a heating mantel, over head stirrer, temperature sensor, decanter, and n-butanol feed pump. The top of the decanter was fitted with a condenser to allow the water-n-butanol azeotrope to condense and collect in the decanter. The top n-butanol layer was returned to the column via an overflow tube, and the water collected for weighing.

The base was charged with 150 g DBT, 166.2 g (1 mole) TPA, and 17.6 g (5% by weight of initial charges) MSA catalyst and the mixture was heated. This reaction was held at 150° C. while feeding n-butanol subsurface.

A total of 325 ml of n-butanol was fed subsurface over sixteen hours. A total of 48.2 g of water were removed, theoretical 36 g. After sixteen hours, the pot was clear and reaction complete. The product was purified and gave the following composition by capillary gas chromatography (area percent):

| | |
|---|---|
| 0.07% | Butyl methane sulfonate |
| 0.01% | Diisobutyl terephthalate |
| 0.05% | n-butyl-isobutyl terephthalate |
| 99.82% | Dibutyl Terephthalate |

Example 10

The equipment consisted of a one-liter base fitted with a heating mantel, over head stirrer, temperature sensor, decanter, and n-butanol feed pump. The top of the decanter was fitted with a condenser to allow the water-n-butanol azeotrope to condense and collect in the decanter. The top n-butanol layer was returned to the column via an overflow tube, and the water collected for weighing.

The base was charged with 150 g DBT, 166.2 g (1 mole) TPA, and 35.2 g (10% by weight of initial charges) MSA catalyst, and the mixture was heated. This reaction was held at 150° C. while feeding n-butanol subsurface.

A total of 425 ml of n-butanol was fed subsurface over fourteen hours. A total of 59.3 g of water were removed (theoretical 36 g). After fourteen hours, the pot was clear and reaction complete.

Area percent gas chromatography results for the reaction mixture showed:

| | |
|---|---|
| 8.99% | n-Butanol |
| 14.84% | Butyl Ether |
| 2.33% | Butyl Methane Sulfonate |
| 73.39% | DBT |

Example 11

The equipment consisted of a one-liter base fitted with a heating mantel, over head stirrer, temperature sensor, decanter, and n-butanol feed pump. The top of the decanter was fitted with a condenser to allow the water-n-butanol azeotrope to condense and collect in the decanter. The top n-butanol layer was returned to the column via an overflow tube, and the water collected for weighing.

The base was charged with 150 g DBT, 166.2 g (1 mole) TPA, and 17.6 g (5% by weight of initial charges) MSA catalyst, and 1.0 g activated carbon, and the mixture was heated. This reaction was held at 150° C. while feeding n-butanol subsurface.

A total of 340 ml of n-butanol was fed subsurface over 15.5 hours. A total of 44.5 g of water were removed (theoretical 36 g). After sixteen hours, the pot was clear and reaction complete. The analytical results are as follows:

| | |
|---|---|
| 9.65% | n-Butanol |
| 5.83% | Butyl Ether |
| 1.16% | Butyl Methane Sulfonate |
| 83.13% | DBT |

Example 12

The equipment consisted of a one-liter base fitted with a heating mantel, over head stirrer, temperature sensor, and decanter. The top of the decanter was fitted with a condenser to allow the water-n-butanol azeotrope to condense and collect in the decanter. The top n-butanol layer was returned to the column via an overflow tube, and the water collected for weighing.

The base was charged with 150 g DBT, 166.2 g (1 mole) TPA, and 17.6 g (5% by weight of initial charges) MSA catalyst and the mixture was heated. This reaction was heated to reflux.

This reaction ran for 19 hours removing 20.0 g of water during reaction. After 1.5 hours of reaction, only a trace amount of water had evolved, the base was then cooled to <60° C. The butanol in the decanter was drained (36 ml), then 51 ml of toluene was added to the base to form an azeotrope with the water. Water began slowly evolving. During the reaction the pot temperature increased and more toluene and butanol were added. The pot cleared after 18.5 hours, and was held an additional thirty minutes. The analytical results are as follows:

| | |
|---|---|
| 5.08% | Butanol |
| 10.79% | Toluene |
| 3.28% | Butyl Ether |
| 2.06% | Butyl Methane Sulfonate |
| 78.46% | DBT |

Example 13

The equipment consisted of a one-liter base fitted with a heating mantel, over head stirrer, temperature sensor, decanter, and n-butanol feed pump. The top of the decanter was fitted with a condenser to allow the water-n-butanol azeotrope to condense and collect in the decanter. The top n-butanol layer was returned to the column via an overflow tube, and the water collected for weighing.

The base was charged with 150 g DBT, 166.2 g (1 mole) TPA, and 3.5 g (1% by weight of initial charges) MSA catalyst and the mixture was heated. This reaction was held at 150° C. while feeding n-butanol subsurface. A total of 335 ml of n-butanol was fed subsurface over thirteen and one half hours. A total of 44.4 g of water were removed, theoretical 38 g, the pot was clear and reaction complete. The excess n-butanol was stripped at a pot temperature of 150° C. and 15 mmHg until collection ceased (1 hour). The total weight of material removed was 67.4 g.

The temperature of the residue was adjusted to 80° C. and treated with 2.5% sodium hydroxide, followed by two water washes. The organic layer was then filtered and dried at 150° C., at 1 mmHg for 1 hour. After drying the product, the temperature was adjusted to 90° C. for a color removal treatment using carbon. This material was then vacuum filtered and the filtrate retained as product. The weight of the material retained was 341.7 g (theoretical—428.3 g, including the 150 g initially in the pot). The product analyzed 99.81% DBT by area percent.

Example 14

The equipment consisted of a one-liter base fitted with a heating mantel, over head stirrer, temperature sensor, Dean-Stark trap, and sparge line for subsurface nitrogen feed. The top of the Dean-Stark trap was fitted with a condenser to allow the water-n-butanol azeotrope to condense and collect in the decanter. The top n-butanol layer was returned to the column via an overflow tube, and the water collected for weighing.

The base was charged with 222.4 g (3.0 mole; 50% excess) n-butanol, 166.2 g (1 mole) TPA, and 17.6 g (5% by weight) MSA catalyst. The mixture was heated to reflux while sparging nitrogen subsurface. After 10.1 hours of reaction, the pot cleared and the reaction was complete. Total water removed was 32.1 g (theoretical 36 g).

The material in the pot was stripped of excess n-butanol to a pot temperature of 158° C. at 17 mmHg for one hour. After drying, the material was cooled and washed with 5% sodium hydroxide followed by two water washes. The product was vacuum filtered then dried the filtrate at 150° C. at 1 mmHg for one hour. Cooled this material to 90° C. and treated with carbon to remove color. The product was then filtered and filtrate retained as product. The final weight was 162.7 g (theoretical 278.3 g) and the assay was 99.71% by area percent.

Example 15

The equipment consisted of a one-liter base fitted with a heating mantel, overhead stirrer, temperature sensor, Dean-Stark trap, and sparge line for subsurface nitrogen feed. The top of the Dean-Stark trap was fitted with a condenser to allow the water-n-butanol azeotrope to condense and collect in the decanter. The top n-butanol layer was returned to the column via an overflow tube, and the water collected for weighing.

The base was charged with 222.4 g (3.0 mole; 50% excess) n-butanol, 166.2 g (1 mole) TPA, and 17.6 g (5% by weight) MSA catalyst. The mixture was heated to reflux while sparging nitrogen subsurface. After 13.25 hours of reaction, the pot cleared and the reaction was complete. Total water removed was 33.8 g (theoretical 36 g).

The area percent analysis of the reaction mixture showed:

| | |
|---|---|
| 14.03% | Butanol |
| 2.18% | Butyl Ether |
| 82.91% | DBT |

Example 16

The equipment consisted of a one-liter base fitted with a heating mantel, over head stirrer, temperature sensor, decanter, and n-butanol feed pump. The top of the decanter was fitted with a condenser to allow the water/n-butanol azeotrope to condense and collect in the decanter. The top n-butanol layer was returned to the column via an overflow tube, and the water collected for weighing.

The base was charged with 150 g DBT, 166.2 g (1 mole) TPA, 17.6 g (5% by weight of initial charges) MSA catalyst, and 25 g n-butanol, and the mixture was heated. This reaction was held at 160° C. while feeding n-butanol subsurface.

A total of 295 ml of n-butanol was fed subsurface over 14 hours and 20 minutes. A total of 46.8 g of water was removed (theoretical 36 g). The pot was clear and reaction complete. The analytical results are as follows:

| | |
|---|---|
| 7.04% | n-Butanol |
| 5.96% | Butyl Ether |
| 1.54% | Butyl Methane Sulfonate |
| 85.28% | DBT |

Example 17

The equipment consisted of a one-liter base fitted with a heating mantel, over head stirrer, temperature sensor, Dean- Stark trap, and sparge line for subsurface nitrogen feed. The top of the Dean-Stark trap was fitted with a condenser to allow the water-n-butanol azeotrope to condense and collect in the decanter. The top n-butanol layer was returned to the column via an overflow tube, and the water collected for weighing.

The base was charged with 296.5 g (3.0 mole; 100% excess) n-butanol, 166.2 g (1 mole) TPA, and 17.6 g (5% by weight) MSA catalyst. The mixture was heated to reflux while sparging nitrogen subsurface. After 10.9 hours of reaction, the pot cleared and the reaction was complete. Total water removed was 33.7 g (theoretical 36 g).

The area percent analysis of the reaction mixture showed:

| 68.58% | DBT |
|---|---|
| 30.93% | Butanol |

Example 18

The equipment consisted of a one-liter base fitted with a heating mantel, over head stirrer, temperature sensor, Dean-Stark trap, and sparge line for subsurface nitrogen feed. The top of the Dean-Stark Trap was fitted with a condenser to allow the water-n-butanol azeotrope to condense and collect in the decanter. The top n-butanol layer was returned to the column via an overflow tube, and the water collected for weighing.

The base was charged with 222.4 g (3.0 mole; 50% excess) n-butanol, 166.2 g (1 mole) TPA, and 16.1 g (4% by weight) 95.7% sulfuric acid as catalyst. The mixture was heated to reflux while sparging nitrogen subsurface. After 16 hours of reaction, the pot contained only a small amount of solids. Total water removed was 46 g (theoretical 36 g). The reaction mixture was sampled for analysis by gc area percent:

| 3.92% | Butanol |
|---|---|
| 7.63% | Butyl Ether |
| 85.31% | DBT |

Example 19

The equipment consisted of a one-liter base 31 fitted with a heating mantel 32, over head stirrer 33, temperature sensor 37, 10" Penn State packed column 34, and Dean-Stark trap. The top of the Dean-Stark Trap was fitted with a condenser 36 to allow the water-n-butanol azeotrope to condense and collect in the decanter. The top n-butanol layer was returned to the column via an overflow tube, and the water collected for weighing. (See FIG. 1 for details of the apparatus.)

The base was charged with 296.5 g (4.0 mole; 100% excess) n-butanol, 166.2 g (1 mole) TPA, and 23.1 g (5% by weight) sulfuric acid as catalyst and the mixture was heated to reflux. After 4 hours of reaction, the pot was clear with no solids present. Total water removed was 49 g (theoretical 36 g).

The mixture was allowed to cool then charged to a drop bottom flask. Mixture was then washed with 5% sodium hydroxide. After washing at 80° C. for 30 minutes, stopped agitation and let settle. Decanted the lower aqueous layer (pH 13), with only a slight amount of color in this layer. Washed the organic layer with D.I. water, same conditions as caustic wash, decanted the lower aqueous layer and tested pH (2). Due to the acid content, charged 10 g of sodium hydroxide (~10% solution) to this layer and charged back, performing another caustic wash. Upon settling, decanted the lower aqueous layer (pH 14) and charged D.I. water to the organic layer for a water wash. Upon settling, decanted the lower aqueous layer (pH 3) and performed another D.I. water wash on the organic layer. Upon settling, decanted the lower aqueous layer still having a pH of 3.

Vacuum filtered the organic layer through a glass fiber filter circle covered with Dicalite filter-aid, into a round-bottom flask with a stir bar. The filtrate was set-up for drying with a temperature sensor, stir bar, 3" Vigreux column, condenser, and receiver. The drying conditions were to a pot temperature of 177° C. at 10 mmHg for one hour. The amount of material removed was 80 ml.

The material was cooled to 90° C. and charged carbon to treat for color. This was held for one hour then vacuum filtered through a glass fiber filter circle covered with Dicalite filter-aid. The filtrate was retained as product. This material became hazy upon cooling, re-filtered through a glass fiber filter circle, this appeared to remove most haze.

Analytical results on final product as follows:

| Specific Gravity @ 20/20 C. | 1.0453 | P |
|---|---|---|
| 1.044 to 1.048 | PASS | |
| Specific Gravity @ 25/25 C. | 1.0421 | P |
| DBT, % | 98.04 | P |
| Isomer of DBT, % | 0.07 | P |
| MBTP, % | 0 | P |
| Appearance | PASS | P |
| Refractive Index @ 20 C. | 1.494 | L |
| 1.496 to 1.499 | FAIL | |
| Refractive Index @ 25 C. | 1.494 | P |
| Turbidity, NTU | 0.74 | P |
| <=2.00 | PASS | |
| Acid Number | 0.1837 | L |
| <=0.0200 | FAIL | |
| Visual Color, pcs | 50.42 | L |
| <=15.00 | FAIL | |
| Water, % | 0.0462 | P |
| <=0.1000 | PASS | |

Example 20

The equipment consisted of a one-liter base fitted with a heating mantel, over head stirrer, temperature sensor, 10" Penn State packed column, and Dean-Stark trap. The top of the Dean-Stark Trap was fitted with a condenser to allow the water-n-butanol azeotrope to condense and collect in the decanter. The top n-butanol layer was returned to the column via an overflow tube, and the water collected for weighing.

The base was charged with 296.5 g (4.0 mole; 100% excess) n-butanol, 166.2 g (1 mole) TPA, and 23.1 g (5% by weight) MSA as catalyst and the mixture was heated to reflux. After 4 hours and thirty minutes of reaction, the pot was clear with no solids present. Total water removed was 37.3 g (theoretical 36 g).

Replaced the 10" Penn State packed column with a 3" Vigreux column to strip excess n-butanol. The stripping went to a pot temperature of 145° C. at 8 mmHg in forty-five minutes. The stripping was shut-off because the material had begun darkening.

Charged the pot contents to a drop bottom flask and stirred with 5% sodium hydroxide for thirty minutes for a caustic wash at 80° C. After stir time, allowed the material to settle then decanted the lower aqueous layer (pH 14). Washed the organic layer two more times with D.I. water following the stir times and temperatures above. After washing step complete, vacuum filtered the organic layer through a glass fiber filter circle covered with Dicalite filter-aid.

The filtrate was then dried to a pot temperature of 140° C. at 0.2 mmHg for one hour. The pot contents were then cooled to 90° C. and carbon was charged, stirred at temperature for one hour. When stir time was complete, vacuum filtered material through a glass fiber filter circle covered with Dicalite filter aid and retained filtrate as product. The amount of product retained was 204.1 g (theoretical 278.3 g), the appearance was light amber. The gas chromatography area percent results were as follows:

| | |
|---|---|
| 0.20% | DBT Isomers |
| 99.64% | DBT |

Example 21 (Repeat of Example 19)

The equipment consisted of a one-liter base fitted with a heating mantel, over head stirrer, temperature sensor, 10" Penn State packed column, and Dean-Stark trap. The top of the Dean-Stark Trap was fitted with a condenser to allow the water-n-butanol azeotrope to condense and collect in the decanter. The top n-butanol layer was returned to the column via an overflow tube, and the water collected for weighing.

The base was charged with 296.5 g (4.0 mole; 100% excess) n-butanol, 166.2 g (1 mole) TPA, and 23.1 g (5% by weight) sulfuric acid as catalyst and the mixture was heated to reflux. After 4 hours of reaction, the pot was clear with no solids present. Total water removed was 48.4 g (theoretical 36 g).

The mixture was allowed to cool then charged to a drop bottom flask. Mixture was then washed with 5% sodium hydroxide. After washing at 80° C. for 45 minutes, stopped agitation and let settle. Decanted the lower aqueous layer and measured the pH (12). Charged additional 5% sodium hydroxide to the pot. Stirred the mixture thirty minutes at 80° C. and let settle, decanted lower aqueous layer (pH 14). Washed organic layer with DI water under same conditions, decanted the lower aqueous layer (pH 2). Repeated the DI water wash with the pH measuring (2-3). Vacuum filtered the organic layer through a glass fiber filter circle coated with Dicalite filter-aid.

The filtrate was then set-up for drying using a 3" Vigreux column and vacuum. The material was dried to a pot temperature of 170° C. at 9 mmHg for one hour. The temperature was then adjusted to 90° C. and carbon was charged and stirred for one hour. After stirring time, the material was then vacuum filtered through a glass fiber filter circle coated with Dicalite filter-aid. Haze was present in the filtrate. The material was therefore re-filtered through two glass fiber filter circles. This filtrate was retained as product. The analytical data is as follows:

| | | |
|---|---|---|
| Specific Gravity @ 20/20 C. | 1.0452 | P |
| 1.044 to 1.048 | PASS | |
| Specific Gravity @ 25/25 C. | 1.0404 | P |
| DBT, % | 98.38 | P |
| Isomer of DBT, % | 0.06 | P |
| MBTP, % | 0 | P |
| Appearance | PASS | P |
| Refractive Index @ 20 C. | 1.497 | P |
| LAB 1.496 to 1.499 | PASS | |
| Refractive Index @ 25 C. | 1.495 | P |
| Turbidity, NTU | 0.48 | P |
| LAB <=2.00 | PASS | |
| Acid Number | 0.1455 | L |
| <=0.0200 | FAIL | |
| NaOH ml | 0.89 | P |
| Visual Color, pcs | 40.81 | L |
| <=15.00 | FAIL | |
| Water, % | 0.0514 | P |
| LAB <=0.1000 | PASS | |

Example 22

The equipment consisted of a one-liter base fitted with a heating mantel, over head stirrer, temperature sensor, 10" Penn State packed column, and Dean-Stark trap. The top of the Dean-Stark Trap was fitted with a condenser to allow the water-n-butanol azeotrope to condense and collect in the decanter. The top n-butanol layer was returned to the column via an overflow tube, and the water collected for weighing.

The base was charged with 296.5 g (4.0 mole; 100% excess) n-butanol, 166.2 g (1 mole) TPA, and 23.1 g (5% by weight) sulfuric acid as catalyst and the mixture was heated to reflux. After 4.5 hours of reaction time, the pot was clear with no solids present. Total water removed was 47.8 g (theoretical 36 g).

Charged this material to a drop bottom flask and adjusted the heat to 80° C. At this temperature, 5% sodium hydroxide was charged and stirred for thirty minutes. After time, stopped stirring and let settle, the lower aqueous layer was then decanted (pH14). DI water was then charged to the organic layer and stirred under same conditions for a wash. After time, let settle and decanted the lower aqueous layer, pH (2-3). Repeated one more DI water wash as described.

After decanting, vacuum filtered the organic layer through a glass fiber filter circle coated with Dicalite filter-aid into a round bottom flask. The filtrate was then set-up for stripping excess alcohol and drying from the washes. The stripping and drying took one hour to a pot temperature of 198° C. at 1 mmHg, taking cuts to determine stripping of all low boilers. Below is the stripping process and data:

| Time | Strip Time (hrs) | Base Temp C. | Take-off Temp C. | Take-off Vol. (ml) | Vacuum | Comments |
|---|---|---|---|---|---|---|
| 12:55 | 0.0 | 28 | 24 | <5 | 10.0 | Refluxing, ease down vacuum to 1.0 torr |

-continued

| | | | | | | |
|---|---|---|---|---|---|---|
| 1:25 | 0.5 | 91 | 25 | 87 | 0.8 | Sampled Take-off Cut 1 - 101-01 Wt-64.9 g |
| 1:55 | 1.0 | 171 | 24 | 0 | 1.0 | |
| 2:12 | 1.3 | 187 | 90 | <2 | 1.0 | |
| 2:20 | 1.4 | 196 | 163 | 28 | 1.0 | Sampled Take-off Cut 2 - 101-02 (weight around 25 g, did not mark down exact weight) |
| 2:45 | 1.8 | 198 | 169 | >100 | 1.0 | Sampled Take-off Cut 3 - 101-03 Wt-126.3 g |
| 2:55 | 2.0 | 196 | 169 | 87 | 1.0 | Sampled Take-off Cut 4 - 101-04 Wt-87.3 g; Shut off, very little left in pot. |

| Sample ID | Butanol | Mesityl Oxide | Butyl Ether | Dibutyl Sulfate | DBT | |
|---|---|---|---|---|---|---|
| 100-01 | 23.20% | 0.05% | 15.10% | 0.50% | 58.99% | Final after 4.5 hour reaction time |
| 101-01 | 57.74% | 0.05% | 41.47% | nd | 0.36% | |
| 101-02 | 0.09% | 0.36% | 0.08% | 8.12% | 89.08% | |
| 101-03 | 0.00% | 0.00% | 0.00% | 0.03% | 99.97% | |
| 101-04 | 0.00% | 0.00% | 0.00% | 0.00% | 99.63% | |

Cuts three and four were then added to the material in the pot. This material was then vacuum filtered through a glass fiber filter circle coated with Dicalite filter-aid. This material was sampled to analytical, results as follows:

| | | |
|---|---|---|
| Specific Gravity @ 20/20 C. | 1.0465 | P |
| 1.044 to 1.048 | PASS | |
| Specific Gravity @ 25/25 C. | 1.0433 | P |
| DBT, % | 99.83 | P |
| Isomer of DBT, % | 0.06 | P |
| MBTP, % | 0.00 | P |
| Appearance | PASS | P |
| Refractive Index @ 20 C. | 1.497 | |
| LAB 1.496 to 1.499 | PASS | |
| Refractive Index @ 25 C. | 1.496 | P |
| Turbidity, NTU | 10.9 | L |
| LAB <=2.00 | FAIL | |
| Acid Number | 0.1053 | L |
| LAB <=0.0200 | FAIL | |
| NaOH ml | 0.58 | P |
| Visual Color, pcs | 10 | P |
| LAB <=15.00 | PASS | |
| comment | | |
| Too cloudy to grade color with Hunter meter | | |
| Water, % | 0.0103 | P |
| LAB <=0.1000 | PASS | |

This material was then charged to a drop bottom flask and washed with 2.5% sodium hydroxide at 80° C. for one hour. After time, let material settle and decanted the lower aqueous layer (pH 14). The organic layer was then washed for one hour at 80° C. with DI water. After time, let material settle and decanted the lower aqueous layer (pH 12). This decant was difficult to separate due similar density with water. The organic layer was charged to a round bottom flask and set-up to dry with vacuum and 3" Vigreux column. The material was dried to a pot temperature of 100° C. at 1 mmHg for one hour. Vacuum filtered this material through a glass fiber filter circle coated with Dicalite filter-aid. Filtrate was sent to analytical for turbidity and acid number, results as follows:

| | | |
|---|---|---|
| Turbidity, NTU | 0.52 | P |
| LAB <=2.00 | PASS | |
| Acid Number | 0.0106 | P |
| LAB <=0.0200 | PASS | |

Laboratory observation showed the material as water white and without haze.

Example 23

The equipment consisted of a one-liter base fitted with a heating mantel, over head stirrer, temperature sensor, 10" Penn State packed column, and Dean-Stark trap. The top of the Dean-Stark Trap was fitted with a condenser to allow the water-n-butanol azeotrope to condense and collect in the decanter. The top n-butanol layer was returned to the column via an overflow tube, and the water collected for weighing.

The base was charged with 296.5 g (4.0 mole; 100% excess) n-butanol, 166.2 g (1 mole) TPA, and 13.9 g (3% by weight) sulfuric acid as catalyst and the mixture was heated to reflux. After 4.5 hours of reaction time, the pot was clear with no solids present. Total water removed was 51.5 g (theoretical 36 g).

The pot contents were then charged to a drop bottom flask and washed with 5% sodium hydroxide at 80° C. for 30 minutes. After time, let settle and decanted the lower aqueous layer (pH12). To the organic layer, two water washes were performed at 80° C., decanting the aqueous layer after each wash. The pH for the first water wash was 3 and the second was 2. After the final decant, vacuum filtered the organic material through a glass fiber filter circle coated with Dicalite filter-aid.

Set-up filtrate for distillation using a 10" Penn State packed column initially, then going to a 3" Vigreux column. The distillation data is as follows:

| Time | Base Temp C. | Take-off Temp C. | Take-off Vol. (ml) | Vacuum, Torr | Comments |
|---|---|---|---|---|---|
| 10:00 | 20 | 24 | 0 | 0.8 | Began heating, material refluxing at room temperature |
| 10:30 | 140 | 24 | 90 | 0.8 | Cut #1 - 103-01 wt-74.4 g |
| 11:00 | 175 | 24 | 0 | 0.8 | |
| 11:10 | 187 | 51 | 0 | 0.9 | Take-off temperature increasing |
| 11:20 | 191 | 151 | 7 | 1 | Cut #2 - 103-02 Wt-6.7 g, cooled down, at a take-off temperature of 151 C., a greater amount of material began coming over. Shut off to replace column with 3" Vigreux column. |
| 12:30 | 93 | 24 | 0 | 1 | Began heating using a 3" Vigreux column |
| 1:00 | 168 | 152 | <2 | 0.8 | Material began coming over |
| 1:30 | 171 | 161 | 142 | 1 | |
| 1:50 | 169 | 156 | 230 | 1 | Shut off; Take-off- 103-03 Wt-237.0 g |

| Sample ID | Mesityl Oxide | Butyl Ether | Dibutyl Sulfate | DBT | |
|---|---|---|---|---|---|
| 102-01 | 29.71% | nd | 9.50% | 0.15% | 59.86% Final after reaction, 5.5 hours using 3% H2SO4 |
| 103-01 | 75.63% | nd % | 23.93% | nd | 0.36% Cut #1 |
| 103-02 | 1.02% | 0.20% | 0.47% | 3.76% | 88.44% Cut #2 |
| 103-03 | 0.04% | nd | 0.07% | 0.02% | 99.87% Final take-off (goodie) |

Overnight 103-03 became slightly hazy with small amount of solids on the bottom. This was filtered through glass fiber filter paper at room temperature, the haze was removed. Acid number on this material was 0.003, specification limit is <0.020.

The invention has been described in detail with particular reference to preferred embodiments thereof, but it will be understood that variations and modifications can be effected within the spirit and scope of the invention.

We claim:

1. A process for the preparation of di-n-butyl terephthalate, comprising:
    contacting terephthalic acid with butanol in the presence of a catalyst in a reactor, and
    removing water via a fractionation column fitted to the reactor,
    wherein the total pressure is maintained at about atmospheric pressure,
    the temperature is maintained at about 110° to 220° C.,
    catalyst is selected from the group consisting of methane sulfonic acid, sulfuric acid, methane disulfonic acid, butane sulfonic acid, perfluorobutane sulfonic acid, and mixtures thereof, and
    the catalyst is present in amount of from about 3% to about 15% by weight.

2. The process according to claim 1, wherein the fractionation column has between 2 to 35 stages.

3. The process according to claim 2, wherein the fractionation column has between 3 to 6 stages.

* * * * *